United States Patent [19]

Van der Knaap

[11] Patent Number: Plant 6,096

[45] Date of Patent: Feb. 2, 1988

[54] CHRYSANTHEMUM PLANT NAMED MON AMI

[75] Inventor: Jacques C. M. Van der Knaap, De Lier, Netherlands

[73] Assignee: Fides, Handelskwekerij, De Lier, Netherlands

[21] Appl. No.: 820,785

[22] Filed: Jan. 22, 1986

[51] Int. Cl.[4] ..... A01H 5/00

[52] U.S. Cl. ..... Plt./77

[58] Field of Search ..... Plt./77

*Primary Examiner*—James R. Feyrer

*Attorney, Agent, or Firm*—Schwartz, Jeffery, Schwaab, Mack, Blumenthal & Evans

[57] ABSTRACT

A Chrysanthemum plant named Mon Ami particularly characterized by its decorative capitulum type; white ray floret color; and, diameter across face of capitulum of 70 mm.

1 Drawing Figure

1

The present invention comprises a new and distinct cultivar of Chrysanthemum, botanically known as *Dendranthema morifolium,* Ramat., previously *Chrysanthemum morifolium,* Ramat., and referred to by the cultivar name Mon Ami.

Mon Ami was originated from a spontaneous mutation of the unpatented cultivar Pink Pompon. Mon Ami was discovered and selected as one flowering plant within a group of flowering plants of the cultivar Pink Pompon by Jacques C. M. Van der Knaap in April of 1981 in a controlled environment in De Lier, The Netherlands.

The first act of asexual reproduction of Mon Ami was accomplished when vegetative cuttings were taken from the initial selection in August of 1983 in a controlled environment in De Lier, The Netherlands by a technician working under formulations established and supervised by Jacques C. M. Van der Knaap. Horticultural examination of selected units initiated in November of 1981 has demonstrated that the combination of characteristics as herein disclosed for Mon Ami are firmly fixed and are retained through successive generations of asexual reproduction.

Mon Ami has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Mon Ami which, in combination, distinguish this Chrysanthemum as a new and distinct cultivar:

1. Decorative capitulum.
2. White ray floret color with yellowing in center.
3. Diameter across face of capitulum of 70 mm.

Of the many commercial cultivars known to the present inventor, the most similar in comparison to Mon Ami is Pink Pompon, the parent cultivar. In comparison to Pink Pompon, Mon Ami has white petals instead of pink, the center of the flower is less dense and the leaves are a darker green. The response, capitulum form and capitulum type of Mon Ami are similar to those same characteristics of Pink Pompon.

2

The accompanying photographic drawing shows typical inflorescence and foliage characteristics of Mon Ami. The photograph is in black and white, with two flowers being colored to accurately depict ray and disc floret colors.

In the following description, color references are made to The Royal Horticultural Society Colour Chart. The color values were determined between 11:00 a.m. and 12:00 noon in October of 1983 under natural day light at De Lier, The Netherlands.

Classification:

*Botanical.*—*Dendranthema morifolium,* Ramat., cv Mon Ami.

*Commercial.*—Cut pompon.

INFLORESCENCE

A. Capitulum:
- *Form.*—Flat.
- *Type.*—Decorative.
- *Diameter across face.*—70 mm.

B. Corolla of ray florets:
- *Color (general tonality from a distance of three meters).*—White.
- *Color (upper surface).*—RHS 155D, with yellowing of florets in center.

C. Corolla of disc florets: Insignificant.

D. Reproductive organs:
- *Androecium.*—Not present.
- *Gynoecium.*—Present in ray florets; numerous.

PLANT

A. General appearance:
- *Height.*—90 cm.

B. Foliage:
- *Color (upper surface).*—RHS 137C.
- *Color (under surface).*—RHS 138B.
- *Shape.*—Long lobed and serrated.

I claim:

1. A new and distinct Chrysanthemum plant named Mon Ami, as described and illustrated, and particularly characterized by its decorative capitulum type; white ray floret color; and diameter across face of capitulum of 70 mm.

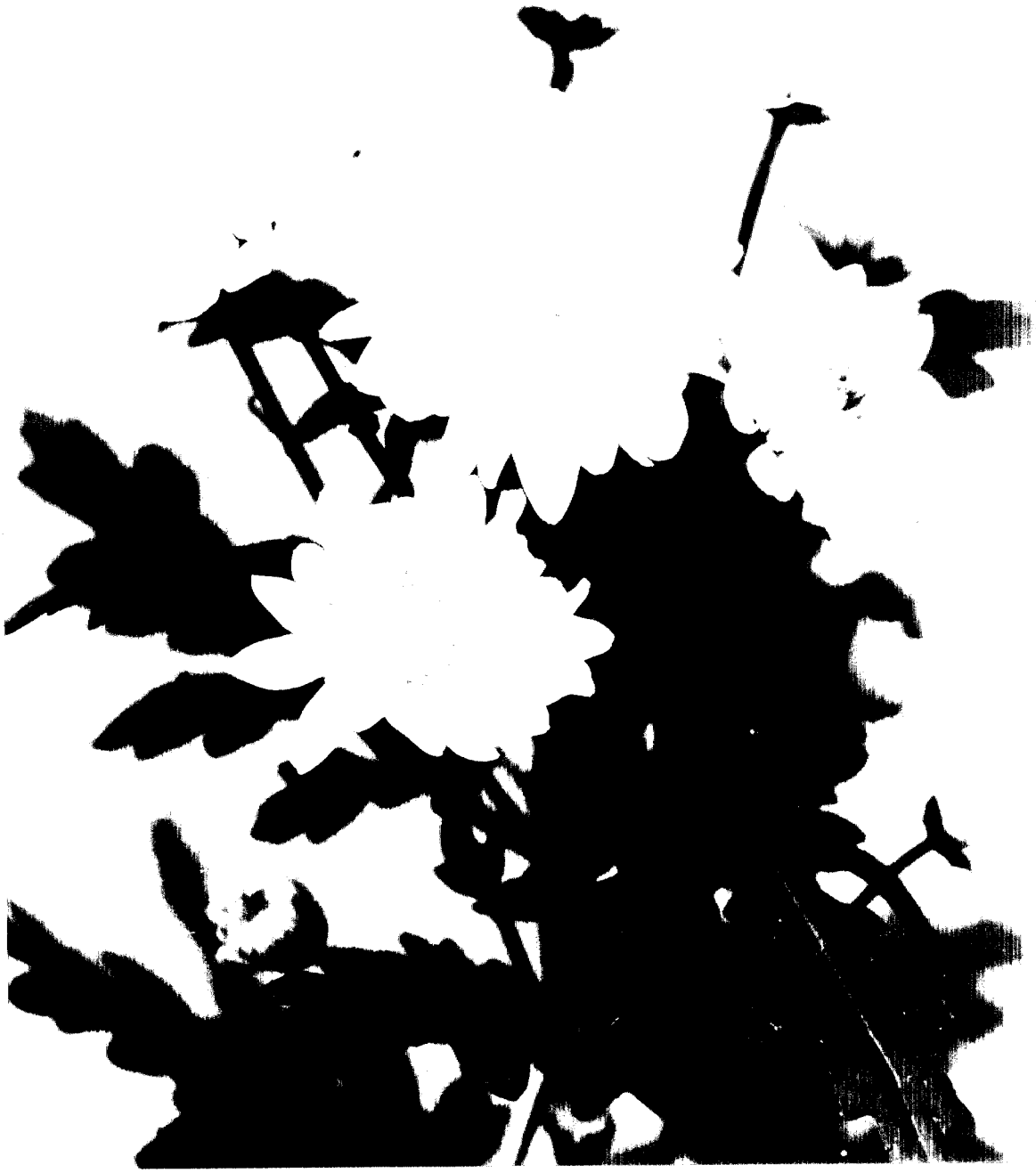

* * * * *